US00PP15477P2

(12) United States Plant Patent
Jarzynka

(10) Patent No.: US PP15,477 P2
(45) Date of Patent: Jan. 11, 2005

(54) ***HYDRANGEA* PLANT NAMED 'LITTLE HONEY'**

(50) Latin Name: *Hydrangea quercifolia*
Varietal Denomination: Little Honey

(76) Inventor: David Jarzynka, 4407 Henderson Blvd., Olympia, WA (US) 98501

( * ) Notice: Subject to any disclaimer, the term of this patent is extended or adjusted under 35 U.S.C. 154(b) by 17 days.

(21) Appl. No.: 10/734,924

(22) Filed: Dec. 11, 2003

(51) Int. Cl.[7] ..... A01H 5/00
(52) U.S. Cl. ..... Plt./250
(58) Field of Search ..... Plt./250

*Primary Examiner*—Kent Bell

(57) ABSTRACT

A new cultivar of *Hydrangea* plant named 'Little Honey' that is characterized by compact spreading habit, panicles of white flowers in summer, golden-chartreuse foliage in summer that turns scarlet in fall, and red stem color in winter. In combination these traits set 'Little Honey' apart from all other existing varieties of *Hydrangea* known to the inventor.

5 Drawing Sheets

Genus: *Hydrangea.*
Species: *quercifolia.*
Denomination: Little Honey.

BACKGROUND OF THE INVENTION

The present invention relates to a new and distinct cultivar of *hydrangea* that is grown as an ornamental shrub for its golden charteruse foliage. The new cultivar is known botanically as *Hydrangea quercifolia* and will be referred to hereinafter by the cultivar name 'Little Honey'.

'Little Honey' is a branch sport and was first discovered in 1999 in a cultivated area of Olympia, Wash. The inventor who first discovered 'Little Honey' operates a tissue culture lab in Olympia, Wash., where he produces and transports woody plants worldwide. 'Little Honey' was discovered as an individual branch sport of the parent plant *Hydrangea quercifolia* 'Pee Wee' (unpatented) in an individual crop of *Hydrangea quercifolia* 'Pee Wee' liners. The parent plant 'Pee Wee' is a cultivated dwarf form of the species and is not patented. Selection of 'Little Honey' was based on its unique golden chartreuse colored leaves.

Additionally, a branch sport of the same description was discovered in the United Kingdom the following spring of 2000, and originating from the same tissue cultured liner crop produced in Washington. The plant in Olympia, Wash. was utilized for the asexual reproduction of further plants. The plant discovered in the United Kingdom was returned to Washington for comparison and observation under a two-year post-entry quarantine. Both sports have been determined identical.

The distinguishing traits of 'Little Honey' are golden chartreuse foliage, dwarf habit, exceptional dark scarlet fall leaf color, and red winter stem color. 'Little Honey' is distinguishable from the parent plant by golden chartreuse summer leaf color, superior branching and moderate vigor. The summer foliage color of 'Pee Wee' is towards green (Royal Horticultural Society Colour Chart No. 144A) and the summer foliage color of 'Little Honey' is golden (Royal Horticulatural Society Chart No. 151B). There are no *Hydrangea* varieties in existence, known to the inventor, that compare to the foliage of 'Little Honey'.

The first asexual reproduction of 'Little Honey' was conducted in 2001 in a cultivated area of Olympia, Wash.

The method used for asexual propagation was tissue culture. The characteristics of the new *Hydrangea* cultivar named 'Little Honey' have been determined stable and are reproduced true to type in successive generations. The plant is also propagated by softwood cuttings and has reproduced true to type by this method also.

SUMMARY OF THE INVENTION

The following traits have been repeatedly observed and represent the characteristics of the new *Hydrangea* cultivar 'Little Honey'. These traits in combination distinguish 'Little Honey' from all other commercial varieties known to the inventor. 'Little Honey' has not been tested under all possible conditions and phenotypic differences may be observed with variations in environmental, climatic and cultural conditions, without however, any difference in genotype.

1. *Hydrangea* 'Little Honey' is a dwarf shrub.
2. *Hydrangea* 'Little Honey' exhibits a compact, upright and spreading habit.
3. *Hydrangea* 'Little Honey' exhibits golden chartreuse colored leaves that turn dark scarlet in fall.
4. *Hydrangea* 'Little Honey' exhibits red stems in winter.
5. *Hydrangea* 'Little Honey' is approximately 63 cm. in height and approximately 63 cm. in width at maturity.
6. *Hydrangea* 'Little Honey' performs best in sun or partial shade with well-drained soil ranging in ph from acid to neutral.
7. Propagation of *Hydrangea* 'Little Honey' is accomplished using tissue culture and softwood cuttings.
8. *Hydrangea* 'Little Honey' is used as a background plant in the landscape suitable for use with conifers or other broad-leafed plants.
9. *Hydrangea* 'Little Honey' is hardy in USDA Zones 5–9.
10. *Hydrangea* 'Little Honey' exhibits panicles of white flowers in summer.

BRIEF DESCRIPTION OF THE DRAWINGS

The accompanying five color drawings illustrate the overall appearance of the new cultivar 'Little Honey' showing the colors as true as it is reasonably possible to obtain in colored reproductions of this type. Colors in the photographs may differ from the color values cited in the detailed botanical description, which accurately describe the actual colors of the new variety of *Hydrangea* named 'Little Honey'.

The five drawings illustrate 'Little Honey' at successive stages in its second year of growth from cuttings rooted in the previous (first) year.

The drawing on sheet 1 is a photographic comparison of 'Little Honey' (on the right) and 'Pee Wee' (on the left). The photograph was taken of these plants growing in a greenhouse in Olympia, Wash. State. The plants shown are 15-weeks-old from cuttings.

The drawing on sheet 2 is a photographic representation of the early summer growth of 'Little Honey' showing the naturally compact growth and the typical juvenile oak-leafed foliage of *Hydrangea quercifolia* and the golden chartreuse foliage color of 'Little Honey'. The photograph was taken from a plant grown outside in a 5-litre container in Arroyo Grande, Calif.

The drawing on sheet 3 is a photographic representation of the mid summer growth of 'Little Honey' when grown in a greenhouse in Olympia, Wash. State. It shows the fully dissected foliage of a plant.

The dawing on sheet 4 illustrates a branch inflorescence of late summer growth of 'Little Honey' when grown in a greenhouse in Olympia, Wash. State.

The drawing on sheet 5 illustrates the fall color of the foliage of 'Little Honey' with the inflorescence still extant when grown in a greenhouse in Olympia, Wash. State.

All drawings were made using conventional techniques and although colors may appear different from actual colors due to light reflectance they are as accurate as possible by conventional photography.

BOTANICAL DESCRIPTION OF THE PLANT

The following is a detailed description of 'Little Honey' as grown in an unheated poly tunnel structure in Olympia, Wash. Data was collected in March from a 5-year-old plant in a 4-litre container. The color determinations are in accordance with The 2002 Royal Horticultural Society Colour Chart of The Royal Horticultural Society, London, England, except where general color terms of ordinary dictionary significance are used. The growing requirements are similar to the species.

Botanical classification: *Hydrangea* 'Little Honey'.
Species: *quercifolia.*
Commercial classification: Deciduous dwarf shrub.
Common name: Oak leaf *hydrangea.*
Use: Background plant for the landscape.
Container size: Suggested container sizes are liners and 2-litre containers.
Cultural requirements: Plant in woodland setting, sun to partial shade with regular water and well-drained acidic to neutral soil.
Parentage: *Hydrangea* 'Little Honey' is a branch sport of the parent plant *Hydrangea quercifolia* 'Pee Wee'.
Plant description:

*Bloom period.*—Late spring to early summer.
*Commercial category.*—Dwarf shrub.
*Plant habit.*—Compact, upright and spreading.
*Vigor.*—Moderate.
*Dimensions.*—63 cm in height and 63 cm in width in a 4-litre container.
*Hardiness.*—USDA Zones 5–9.
*Root system.*—Fibrous.
*Propagation.*—Propagation is accomplished using tissue culture and softwood cuttings.
*Time to develop root.*—6–8 weeks or less depending on the condition of stock plants and season; 3–4 weeks under ideal conditions.
*Air temperature for rooting.*—21–24° Centigrade.
*Crop time.*—A branched liner can be produced in 15 weeks and a blooming 2-litre container plant can be produced in 120 weeks.
*Disease and pest susceptibility.*—May be susceptible to aphids or spider mites but plant is not particularly susceptible to any pest or disease.
*Special growing problems.*—Susceptible to leaf burn if placed in hot reflected sun or if the amount of fertilizer used is too high.
*Special growing requirements.*—No requirements however light shade is best in warm regions. More exposure to sunlight can enhance fall color.

Stem:

*Trunk shape.*—Cylindrical.
*Main trunk dimensions.*—1.50 cm. in diameter and 45 cm. in height.
*Trunk surface.*—Lanate.
*Trunk color.*—165A.
*Bark color on main trunk.*—137C.
*Bark texture.*—Flaking.
*Branch shape* (*mature and young*).—Cylindrical.
*Mature branch dimensions* (*average*).—35 cm. in length and 1 cm in diameter.
*Mature branch color.*—Colors 174B and 165A are both individually present on individual mature branches.
*Mature branch surface.*—Furrowed.
*Young branch color.*—165A.
*Winter stem color* (*mature stems*).—183C.
*Young branch dimensions* (*average*).—26 cm. in length and 0.25 cm. in diameter.
*Young branch surface.*—Lanate.
*Branching habit.*—Central trunk with superior divergent branching.
*Internode length.*—5 cm. between nodes.

Foliage:

*Type.*—Deciduous.
*Arrangement.*—Opposite.
*Mature leaf shape.*—Palmate.
*Young leaf shape.*—Closer to ovate.
*Leaf margins* (*young and mature*).—Serrate.
*Division.*—Simple.
*Apex* (*young and mature leaf*).—Acute.
*Base* (*young and mature leaf*).—Cuneate.
*Venation pattern.*—Pinnate.
*Young leaf vein color* (*adaxial and abaxial surfaces*).—151C.
*Mature leaf vein color* (*adaxial and abaxial surfaces*).—151C.
*Attachment* (*mature and young leaf*).—Petiolate.
*Petiole color* (*young leaf*).—151C.
*Petiole color* (*mature leaf*).—151C.
*Petiole shape* (*mature and young leaf*).—Sulcate.
*Petiole surface* (*mature and young leaf*).—Lanate.
*Petiole dimensions* (*mature leaf*).—8 cm. in length and 3 mm. in width.

*Petiole dimensions* (*young leaf*).—1.25–3 cm. in length and 2 mm. in width.
*Mature and young leaf surfaces* (*abaxial*).—Lanate.
*Young leaf surfaces* (*adaxial*).—Pubescent.
*Mature leaf surfaces* (*adaxial*).—Slightly puberulent.
*Mature leaf dimensions.*—9–16 cm. in width and 10–18 cm. in length.
*Young leaf dimensions.*—2 cm. in width and 4 cm. in length.
*Color of mature leaf* (*abaxial and adaxial surfaces*).—151B.
*Color of young leaf* (*abaxial and adaxial surfaces*).—151B.
*Fall color* (*adaxial and abaxial surfaces of mature leaves*).—The predominant color of individual leaves is 183C. A combination of the colors N170B and 182B can also be found on some individual leaves.
*Fragrance.*—None observed.

Flowers:

Inflorescence:
*Inflorescence type.*—Panicle.
*Inflorescence shape.*—Conical.
*Inflorescence dimensions.*—Dimensions range from 22–23 cm. in length and 9–12 cm. in diameter.
*Typical number of flowers per inflorescence.*—Typical number of flowers per panicle ranges from 60–100.
*Typical number on inflorescences per plant.*—Typical number of panicles per individual 4-litre container plant ranges from 5–12.
*Lastingness of individual flowers.*—Individual flowers last from 2–4 weeks on individual panicles.
*Lastingness of inflorescence.*—An individual inflorescence lasts 3–4 weeks on an individual plant.

Pedicel:
*Pedicel dimensions.*—4–6 cm. in length and 1 mm. in diameter.
*Pedicel color.*—N144A.
*Pedicel shape.*—Cylindrical.
*Pedicel surface.*—Puberulent.

Peduncle:
*Peduncle shape.*—Cylindrical.
*Peduncle color.*—Lower one-third is 165A and upper two-thirds is 137A.
*Peduncle dimensions.*—Peduncle is 24 cm. in length and 0.20 cm. in diameter.
*Peduncle surface.*—Pubescent.

Bud:
*Bud shape.*—Clavate.
*Bud color.*—155A.
*Bud dimensions.*—Bud dimensions range from 4 mm–6 mm in length and from 1.5 mm–3 mm in width.

Flower:
*Flower aspect.*—Facing upward and outward.
*Flower shape.*—Rotate.
*Flower arrangement.*—Whorled.
*Flower dimensions.*—From 1.5 mm to 2.0 mm in diameter.
*Flower color* (*adaxial and abaxial surfaces*).—Individual flowers on an individual inflorescence range in color between and including 155A and 160D.
*Sexuality.*—Bisexual.

Petals: Petals not observed.

Sepals.
*Number.*—Four in number.
*Venation pattern.*—Pinnate.
*Vein color* (*adaxial and abaxial surfaces*).—156D.
*Sepal surfaces* (*adaxial and abaxial surfaces*).—Glabrous.
*Sepal appearance.*—Irridescent.
*Sepal shape.*—Closest to obdeltoid.
*Sepal apex.*—Obtuse.
*Sepal base.*—Cuneate.
*Sepal dimensions.*—Sepal width is 6 mm. in width and ranges in length from 8–10 mm.
*Fused or unfused.*—Unfused.
*Sepal margin.*—Entire.
*Sepal color* (*adaxial and abaxial surface*).—Sepals range in color from 155A to 160D.

Reproductive organs:
*Stamens.*—stamens.
*Stamen color.*—155A.
*Stamen dimensions.*—3 mm. in length and 0.25 mm. in width.
*Anther color.*—155A.
*Anther dimensions.*—0.50 mm. in length and 0.25 mm. in width.
*Quantity of pollen.*—Small amount.
*Pollen color.*—155C.
*Ovary.*—None observed to date.
*Pistil.*—None observed to date.

Seed production: No seed production has been observed to date.

It is claimed:

1. A new and distinct cultivar of *Hydrangea* plant named 'Little Honey' as described and illustrated herein.

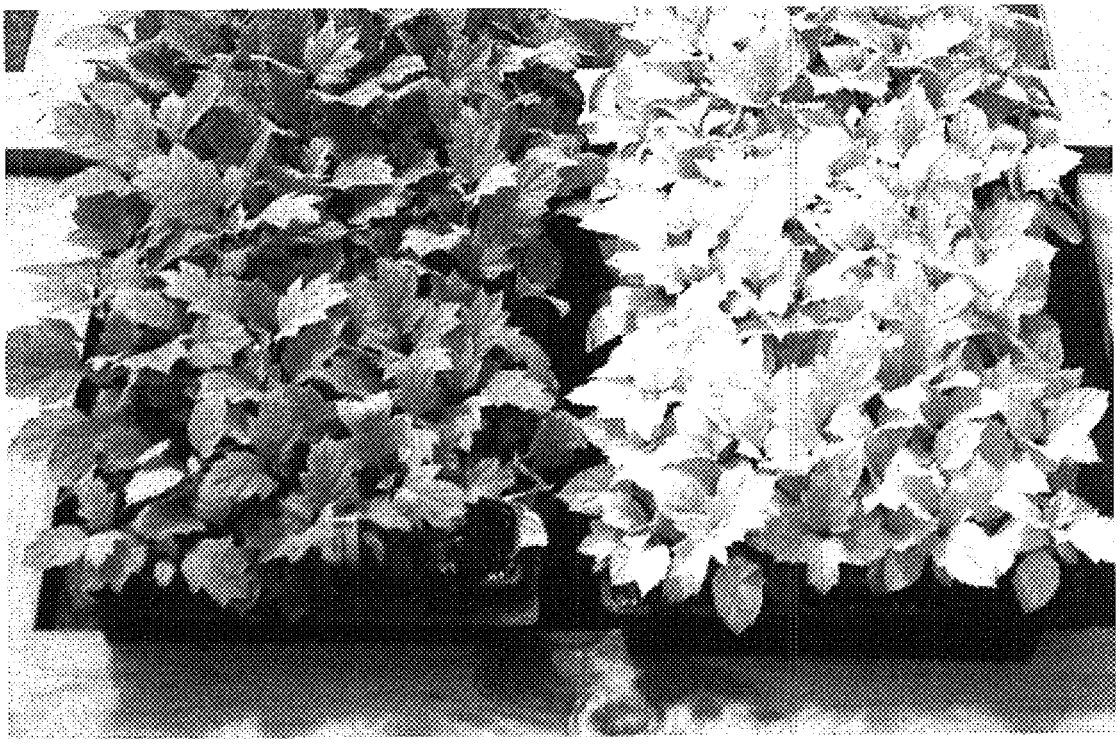

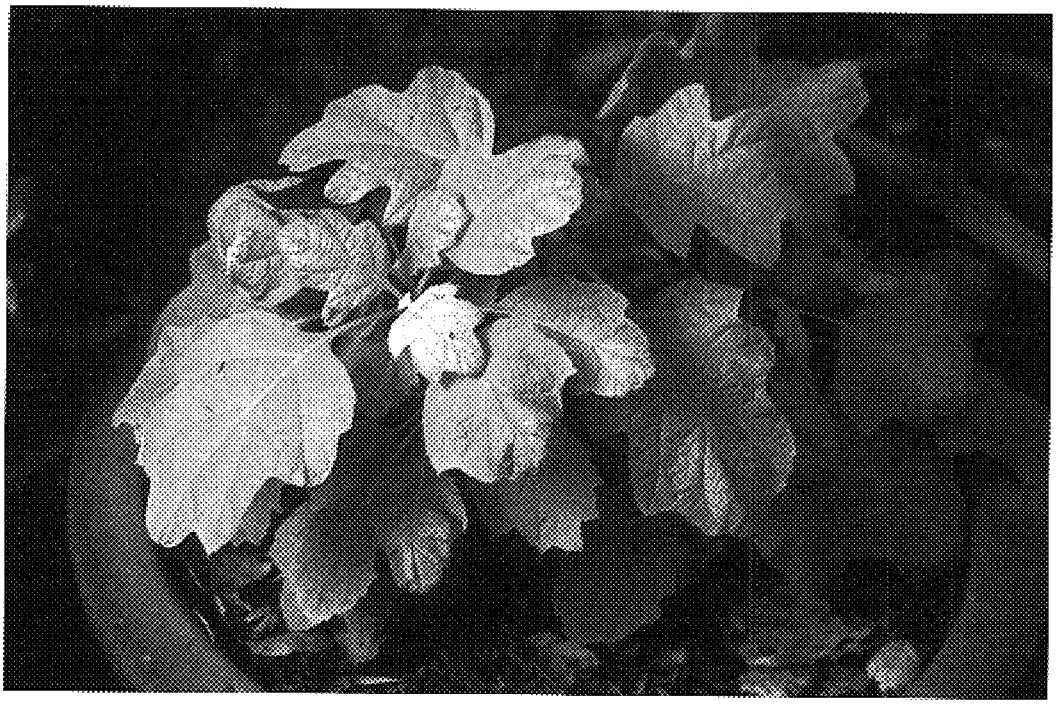

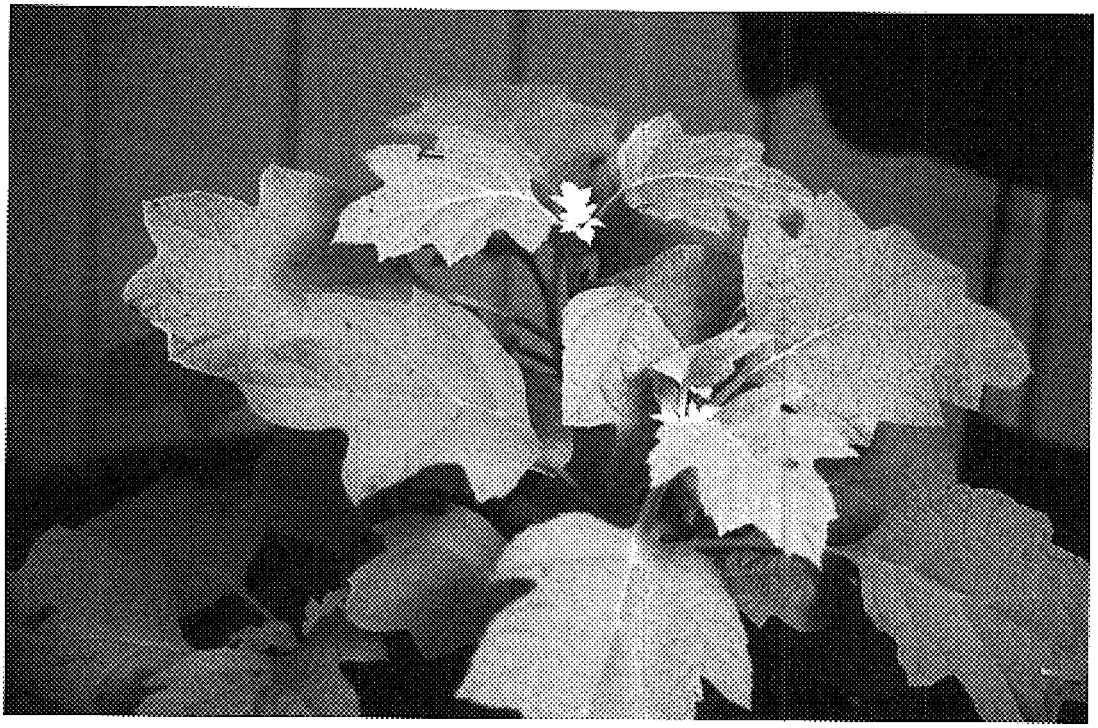

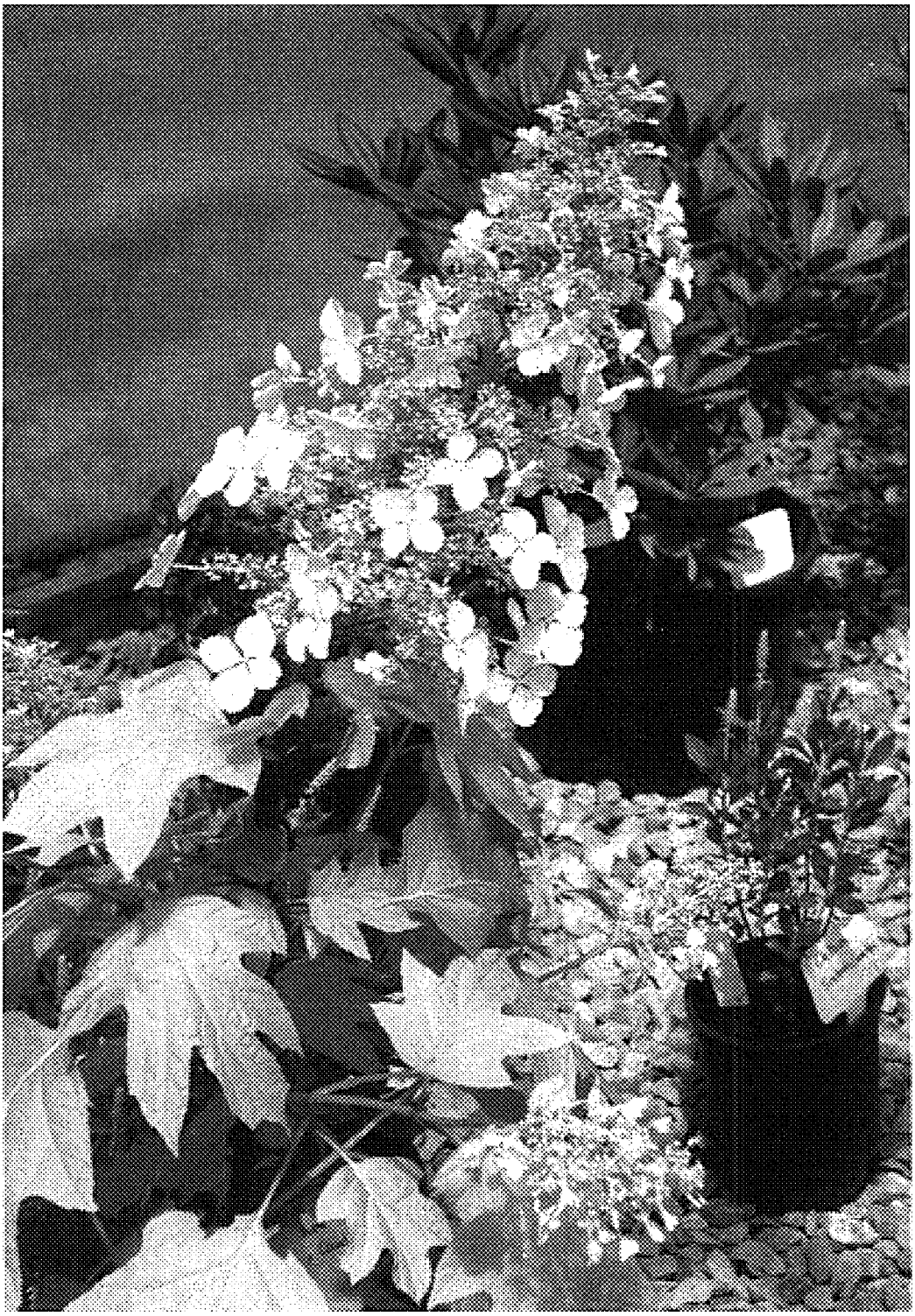

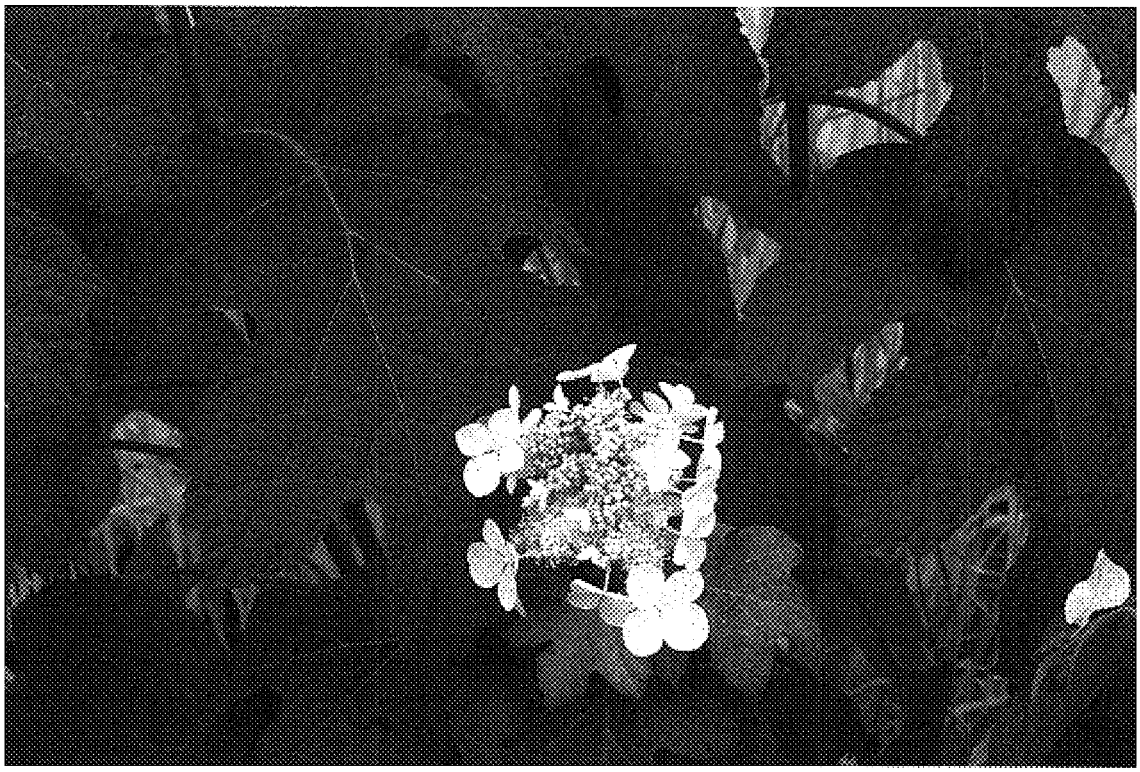

* * * * *